(12) United States Patent
Sun et al.

(10) Patent No.: US 8,563,721 B2
(45) Date of Patent: Oct. 22, 2013

(54) MORPHINAN DERIVATIVES AND PREPARATION METHODS THEREOF

(75) Inventors: Huafu Sun, Chongqing (CN); Jie Luo, Chongqing (CN); Wenrun Ye, Chongqing (CN); Jie Deng, Chongqing (CN); Bo Lin, Chongqing (CN); Chunyan Dan, Chongqing (CN); Bin Fan, Chongqing (CN)

(73) Assignee: Chongqing Pharmaceutical Research Institute Co., Ltd., Chongqing (CN)

( * ) Notice: Subject to any disclaimer, the term of this patent is extended or adjusted under 35 U.S.C. 154(b) by 240 days.

(21) Appl. No.: 13/000,200

(22) PCT Filed: Jun. 19, 2009

(86) PCT No.: PCT/CN2009/072350
§ 371 (c)(1),
(2), (4) Date: Dec. 20, 2010

(87) PCT Pub. No.: WO2009/152776
PCT Pub. Date: Dec. 23, 2009

(65) Prior Publication Data
US 2011/0112297 A1  May 12, 2011

(30) Foreign Application Priority Data

Jun. 20, 2008  (CN) .......................... 2008 1 0069852

(51) Int. Cl.
*C07F 7/02* (2006.01)
*C07D 489/08* (2006.01)
(52) U.S. Cl.
USPC .................... 546/14; 546/44; 546/45; 546/15
(58) Field of Classification Search
USPC ......................................... 546/44, 45, 14, 15
See application file for complete search history.

(56) References Cited

U.S. PATENT DOCUMENTS

| 3,332,950 A | 7/1967 | Blumberg et al. |
| 4,161,597 A | 7/1979 | Olofson et al. |
| 4,176,186 A | 11/1979 | Goldberg et al. |

FOREIGN PATENT DOCUMENTS

| CN | 1665819 A | 9/2005 |
| GB | 981046 | 1/1965 |
| JP | 41-003702 | 8/1963 |
| WO | WO 2004/043964 A2 | 5/2004 |
| WO | WO 2006/127899 A2 | 11/2006 |
| WO | WO 2008/064353 A2 | 5/2008 |
| WO | WO 2008/070462 A2 | 6/2008 |

OTHER PUBLICATIONS

Lattanzi et al., "Synthesis and biological evaluation of 14-Alkoxymorphinanas. 22.[1] Influence of the 14-Alkoxy group and the substitution in position 5 in 14-Alkoxymorphinan-6-ones on in vitro and in vivo activities," *J. Med.Chem.* (2005) 48: 3372-3378.
Deschamps et al., "7β, 14β-Epoxyhydrocodone-6,6-dimethoxyketal: an unusual oxteane-containing opioid," *Acta Cryst.* (2004) E60: o331-o333.
Meredith et al., "Isolation and synthesis of 2-chloro-10-α-hydroxynaltrexone, a new naltrexone degradant," *Tetrahedron Letters* (2003) 44: 7381-7384.
McCurdy et al., "Investigation of phenolic bioisosterism in opiates: 3-sulfonamido analogues of naltrexone and oxymorphone," *Organic Letters* (2000) 2 (6): 819-821.
Kalinin et al., "Letters to the Editor: 14β-hydroxy-17-nor-17-phenyldihydrocodeinone ethylene ketal, the first N-aryl derivative of morphine alkaloids," *Russian Chemical Bulletin* (1997) 46 (4): 845.

*Primary Examiner* — Charanjit Aulakh
(74) *Attorney, Agent, or Firm* — Merchant & Gould P.C.

(57) ABSTRACT

The present invention relates to morphinan derivatives and preparation methods thereof, especially to ketal hydroxyl protected compounds of morphinan derivatives and preparation method thereof, and to a method for preparing corresponding alkylated morphinan derivatives by using the ketal hydroxyl protected compounds as intermediates, and more especially to a ketal hydroxyl protected compound of methylnaltrexone as intermediate for preparing methylnaltrexone and a method for preparing methylnaltrexone through said intermediate.

18 Claims, No Drawings

MORPHINAN DERIVATIVES AND PREPARATION METHODS THEREOF

This application is a National Stage Application of PCT/CN2009/072350, filed Jun. 19, 2009, which claims benefit of Serial No. 200810069852.0, filed Jun. 20, 2008 in P.R. China and which applications are incorporated herein by reference. To the extent appropriate, a claim of priority is made to each of the above disclosed applications.

TECHNICAL FIELD

The present invention relates to morphinan derivatives and preparation methods thereof, and also relates to ketal hydroxyl protected compounds of morphinan derivatives and a method for preparing the same, especially to a method for preparing corresponding alkylated morphinan derivatives by using the ketal hydroxyl protected compounds as intermediates.

BACKGROUND OF THE INVENTION

Morphinan alkaloid such as R-methylnaltrexone (abbreviated as MNTX) of the following structural formula:

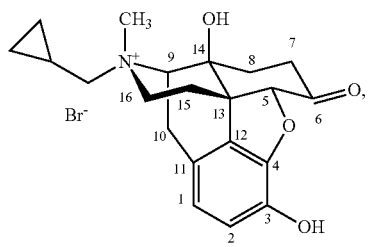

as a μ-receptor antagonist in clinic, has useful pharmacological properties. It mainly binds to the receptors located at peripheral of gastrointestinal tract, acts as an antagonist, and can effectively alleviate unwanted side effects such as constipation and nausea during opiate treatment. Meanwhile, due to its ionic charge, it cannot cross blood-brain barrier and enter into central nervous system, so that the pain relief caused by the central activity of opiate will not be blocked by the existing quaternary derivatives.

The methods for preparing methylnaltrexone have been reported in earlier documents. For example, U.S. Pat. No. 4,176,186 and WO2004043964 disclose a method for preparing methylnaltrexone. The reaction scheme is as follows:

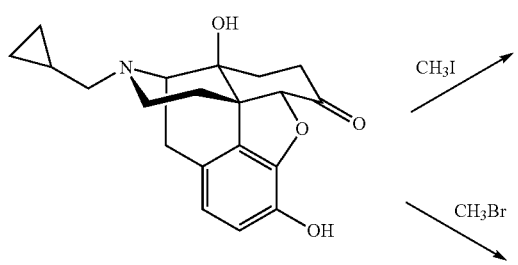

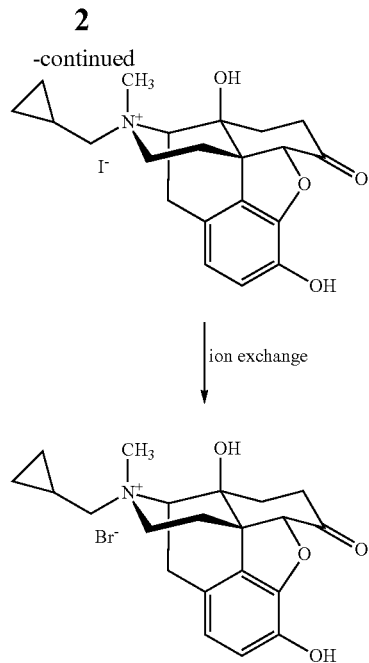

U.S. Pat. No. 4,176,186 discloses that methylnaltrexone is prepared by reacting naltrexone as raw material with methyl iodide in acetone as solvent in a closed vessel at 70° C. for 4 days to produce an iodide of MNTX after quaternization, and then performing an ion exchange. The two-step reaction has a yield of about 54%. The disadvantages of this method lie in that the raw material would not react completely; the raw material would form a salt and precipitate out during the process of the reaction; a qualified product would not be not ease to be obtained even after refining; moreover; and phenol alkylation byproducts would be generated.

WO2004043964 discloses a method for preparing methylnaltrexone by reacting naltrexone as raw material with methyl bromide under normal pressure in a dipolar solvent such as NMP (N-methyl-pyrrolidinone), and then performing a quaternization reaction. Although the problem that the raw material tends to precipitate when acetone is used as the solvent has been overcome by this method, and a good result has been obtained by performing the reaction under normal pressure or slight pressurization, it still has some disadvantages, for example: the raw material would not react completely; a phenol alkylation byproduct tends to occur; the reaction product usually is not a solid, but have to be obtained by forming a sodium salt and then subjecting to precipitation, and then acidization, which renders the refining a relatively low yield and complex operation for industrialization.

In order to overcome the drawback of the generation of phenol alkylation byproduct, WO2006127899 describes that methylnaltrexone is prepared by firstly protecting the phenol group with isobutyryl chloride, quaternizing with methyl iodide, and then hydrolysis and ion exchange. The reaction scheme is as follows:

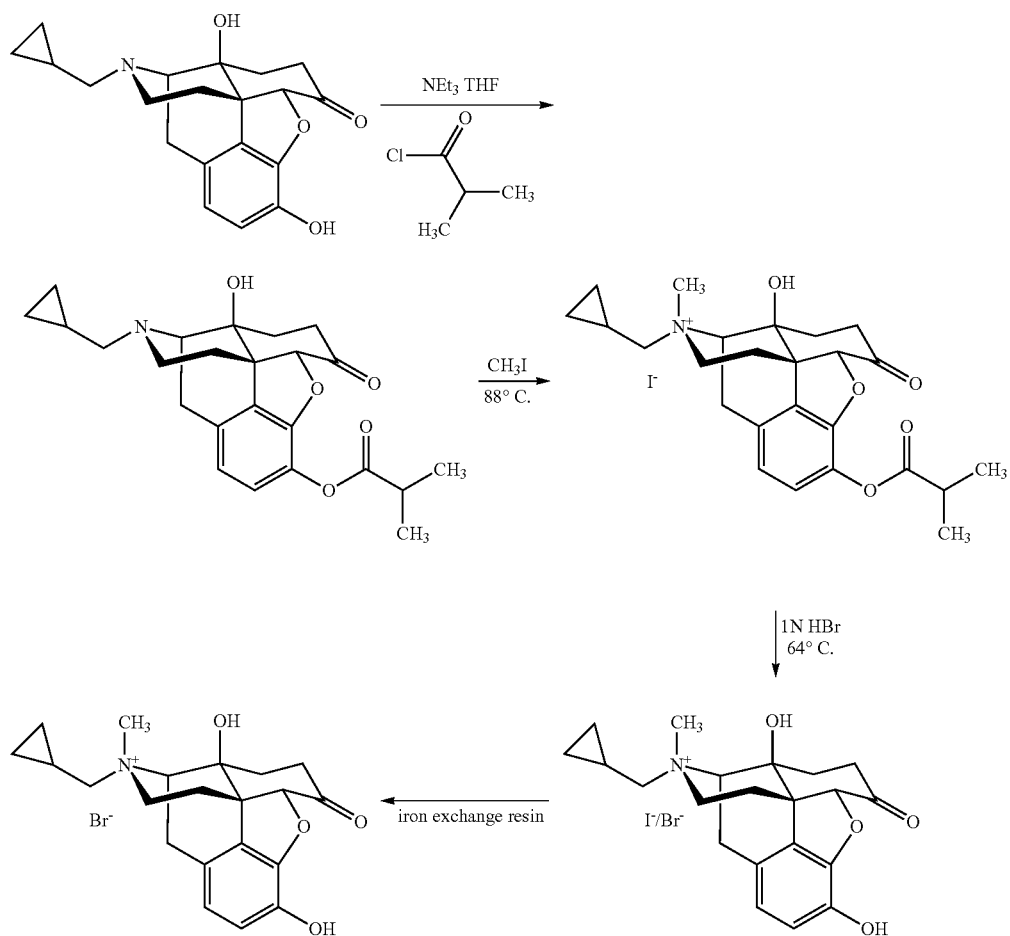

Although the drawback that a phenol alkylation byproduct tends to occur has been overcome by this method, it still has shortages. For example, the esterification yield is not high (76.8%), and it requires to be purified by a column; when methyl iodide alone as a solvent is used for the quaternization reaction, it must be performed in a closed pressure vessel, and also requires to be purified by a column; the hydrolysis lasts for a long time, and the product is not well solidified with many impurities therein, thus the product has low purity and needs repeated refining. Furthermore, the amount of its isomer, that is, S-methylnaltrexone, is relatively high (2.69%) and the total yield in the case of such purity is only 38.5%. To provide a product with a higher purity, crystallization has to be repeated 4 or more times. Moreover, it imposes higher requirements on equipment for industrial production, the operation thereof is complicated, and multi-crystallization results in a decrease of yield and an increase of cost.

Therefore, there remains a need for more morphinan alkaloid derivatives and methods for preparing the same, especially for a more effective and more economic method for preparing R-methylnaltrexone.

SUMMARY OF THE INVENTION

In one aspect, the present invention provided a compound of Formula 1(N-alkyl quaternary derivative of tertiary morphinan alkaloid)

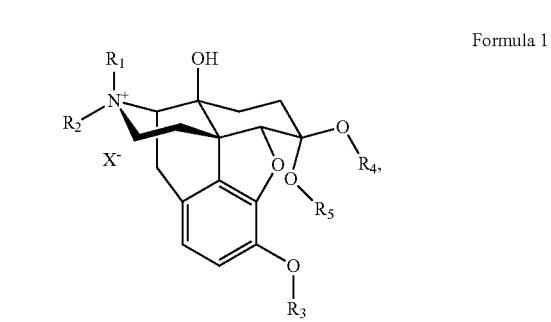

Formula 1 wherein $R_1$ and $R_2$ are each independently a hydrocarbyl or a substituted hydrocarbyl, such as a substituted or unsubstituted $C_{1-20}$ hydrocarbyl, especially a substituted or unsubstituted $C_{1-6}$ hydrocarbyl, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl, $R_3$ is a hydroxyl protecting group or hydrogen, $R_4$ and $R_5$ are each independently a substituted or unsubstituted hydrocarbyl, such as a substituted or unsubstituted $C_{1-20}$ hydrocarbyl, especially a substituted or unsubstituted $C_{1-6}$ hydrocarbyl, or form a substituted or unsubstituted 5- or 6-membered ring together with the adjacent "—O—C—O—" moiety, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl, $X^-$ is an anion.

In one embodiment of the invention, $R_1$ and $R_2$ in the Formula 1 can each independently be methyl, ethyl, propyl, allyl (—$CH_2CH$=$CH_2$), cyclopropylmethyl or chloroallyl, preferably methyl; more preferably, $R_2$ is cyclopropylmethyl when $R_1$ is methyl, or $R_2$ is methyl when $R_1$ is cyclopropylmethyl.

In one embodiment of the invention, the hydroxyl protecting group represented by $R_3$ in the Formula 1 is a substituted or unsubstituted hydrocarbyl, acyl or silyl, such as a substituted or unsubstituted $C_{1-20}$ hydrocarbyl, a substituted or unsubstituted $C_{1-20}$ acyl or a substituted or unsubstituted $C_{1-20}$ hydrocarbyl silyl, especially a substituted or unsubstituted $C_{1-6}$ hydrocarbyl, a substituted or unsubstituted $C_{1-6}$ acyl or a substituted or unsubstituted $C_{1-6}$ hydrocarbyl silyl, wherein the substituent can each independently be selected from the group consisting of fluorine, chlorine, bromine or $C_{1-6}$ hydrocarbyl, which hydrocarbyl can be any suitable alkyl group, cycloalkyl, polycyclic alkyl, alkenyl, cycloalkenyl, alkynyl or aryl.

In one embodiment of the invention, $R_3$ in the Formula 1 is trimethylsilyl, triethylsilyl, phenyldimethylsilyl, tert-butyldimethylsilyl, tert-butyldiphenylsilyl, or triisopropylsilyl.

In one embodiment of the invention, $R_4$ and $R_5$ in the Formula 1 can each independently be a ketal protecting group, preferably $C_{1-6}$ hydrocarbyl and $C_{6-10}$ aromatic $C_{1-6}$ hydrocarbyl, which hydrocarbyl can be any suitable alkyl, cycloalkyl, polycyclic alkyl, alkenyl, cycloalkenyl, alkynyl or aryl, and more preferably, $R_4$ and $R_5$ are each independently methyl or ethyl, or $R_4$=$R_5$=—$CH_2$—, with $R_4$ and $R_5$ together forming an ethylidene radical.

In one embodiment of the invention, $X^-$ in the Formula 1 is an anion, such as fluoride, chloride, bromide, iodide, nitrate, sulfate, methanesulfonate, phenylsulfonate, p-toluenesulfonate, trifluoro-methanesulfonate or phosphate, or a combination thereof; typically, $X^-$ can be a halide ion, and is preferably methanesulfonate, iodide, bromide, chloride, fluoride, or a combination thereof.

In another aspect, the present invention is to provide a compound of Formula 2 (tertiary morphinan derivative),

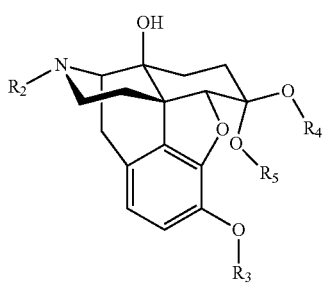

Formula 2 wherein $R_2$ is a hydrocarbyl or substituted hydrocarbyl, such as a substituted or unsubstituted $C_{1-20}$ hydrocarbyl, particularly a substituted or unsubstituted $C_{1-6}$ hydrocarbyl, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl, $R_3$ is a hydroxyl protecting group or hydrogen, $R_4$ and $R_5$ are each independently a substituted or unsubstituted hydrocarbyl, such as a substituted or unsubstituted $C_{1-20}$ hydrocarbyl, particularly a substituted or unsubstituted $C_{1-6}$ hydrocarbyl, or form a substituted or unsubstituted 5- or 6-membered ring together with the adjacent "—O—C—O—" moiety, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl.

In one embodiment of the invention, $R_2$ in the Formula 2 can be methyl, ethyl, propyl, allyl (—$CH_2CH$=$CH_2$), chloroallyl, cyclopropylmethyl, cyclobutylmethyl or propargyl, and $R_2$ is preferably cyclopropylmethyl.

In one embodiment of the invention, the protected group of hydroxyl represented by $R_3$ in the Formula 2 can be a substituted or unsubstituted hydrocarbyl, acyl or silyl, for example, a substituted or unsubstituted $C_{1-20}$ hydrocarbyl, a substituted or unsubstituted $C_{1-20}$ acyl or a substituted or unsubstituted $C_{1-20}$ hydrocarbyl silyl, particularly a substituted or unsubstituted $C_{1-6}$ hydrocarbyl, a substituted or unsubstituted $C_{1-6}$ acyl or a substituted or unsubstituted $C_{1-6}$ hydrocarbyl silyl, wherein the substituent can each independently be selected from the group consisting of fluorine, chlorine, bromine or $C_{1-6}$ hydrocarbyl, which hydrocarbyl can be any suitable alkyl group, cycloalkyl, polycyclic alkyl, alkenyl, cycloalkenyl, alkynyl or aryl.

In one embodiment of the invention, $R_3$ in the Formula 2 is typically a hindered-type silane protecting group, such as trimethylsilyl, triethylsilyl, phenyldimethylsilyl, tert-butyldimethylsilyl, tert-butyldiphenylsilyl or triisopropyl silyl, and preferably is tert-butyldimethylsilyl.

In one embodiment of the invention, $R_4$ and $R_5$ in Formula 2 are each independently a ketal protecting group, preferably $C_{1-6}$ hydrocarbyl and $C_{6-10}$ aromatic $C_{1-6}$ hydrocarbyl, which hydrocarbyl can be any suitable alkyl, cycloalkyl, polycyclic alkyl, alkenyl, cycloalkenyl, alkynyl or aryl, and more preferably, $R_4$ and $R_5$ are each independently methyl or ethyl, or $R_4$=$R_5$=—$CH_2$—, with $R_4$ and $R_5$ forming an ethylidene radical together.

In one embodiment of the invention, the compound of Formula 2 can be a representative tertiary morphinan alkaloid, which can be selected from the group consisting of 17-(cyclopropylmethyl)-4,5a-epoxy-3,14-dihydroxy-6-(1,3-dioxolan-2-yl)-morphinan (naltrexone ketal), 4,5a-epoxy-3,14-dihydroxy-17-methyl-6-(1,3-dioxolan-2-yl)-morphinan (oxymorphone ketal), 4,5a-epoxy-14-hydroxyl-3-methoxy-17-methyl-6-(1,3-dioxolan-2-yl)-morphinan (oxycodone ketal), 4,5a-epoxy-3,14-dihydroxy-17-(2-propenyl)-6-(1,3-dioxolan-2-yl)-morphinan (naloxone ketal), and preferably naltrexone ketal.

In one embodiment of the invention, the compound of Formula 2 can also be selected from the group consisting of 3-[(tert-butyldimethylsilyl)oxy]-17-(cyclopropylmethyl)-4,5a-epoxy-14-hydroxyl-6-(1,3-dioxolan-2-yl)morphinan (hydroxyl protected compound of naltrexone ketal), 3-[(tert-butyldiphenylsilyl)oxy]-17-(cyclopropylmethyl)-4,5a-epoxy-14-hydroxyl-6-(1,3-dioxolan-2-yl)morphinan (hydroxyl protected compound of naltrexone ketal), 3-[(triisopropylsilyl)oxy]-17-(cyclopropylmethyl)-4,5a-epoxy-14-hydroxyl-6-(1,3-dioxolan-2-yl)morphinan (hydroxyl protected compound of naltrexone ketal), 3-[(tert-butyldimethylsilyl)oxy]-4,5a-epoxy-14-hydroxyl-17-methyl-6-(1,3-dioxolan-2-yl)-morphinan (hydroxyl protected compound of oxymorphone ketal), 3-[(tert-butyldiphenylsilyl)oxy]-4,5a-epoxy-14-hydroxyl-17-methyl-6-(1,3-dioxolan-2-yl)-morphinan (hydroxyl protected compound of oxymorphone ketal), 3-[(triisopropylsilyl)oxy]-4,5a-epoxy-14-hydroxyl-17-methyl-6-(1,3-dioxolan-2-yl)-morphinan (hydroxyl protected compound of oxymorphone ketal), 3-[(tert-butyldimethylsilyl)oxy]-4,5a-epoxy-14-hydroxyl-17-(2-propenyl)-6-(1,3-dioxolan-2-yl)-morphinan (hydroxyl protected compound of naloxone ketal), 3-[(tert-butyldiphenylsilyl)oxy]-4,5a-epoxy-14-hydroxyl-17-(2-propenyl)-6-(1,3-dioxolan-2-yl)-morphinan (hydroxyl protected compound of naloxone ketal) or 3-[(triisopropylsilyl)oxy]-4,5a-epoxy-14-hydroxyl-17-(2-propenyl)-6-(1,3-dioxolan-2-yl)-morphinan (hydroxyl protected compound of naloxoneketal). The hydroxyl protected compound of naltrexone ketal is preferred.

In one embodiment of the invention, the compound of Formula 1 can be a representative N-alkyl quaternary derivative of tertiary morphinan alkaloid, which can be selected from the group consisting of 3-[(tert-butyldimethylsilyl)oxy]-17-(cyclopropylmethyl)-4,5a-epoxy-14-hydroxyl-6-(1,3-dioxolan-2-yl)-N-methylmorphinan iodide (N-methyl quaternary derivative of naltrexone), 3-[(tert-butyldiphenylsilyl)oxy]-17-(cyclopropylmethyl)-4,5a-epoxy-14-hydroxyl-6-(1,3-dioxolan-2-yl)-N-methylmorphinan iodide (N-methyl quaternary derivative of naltrexone), 3-[(triisopropylsilyl)oxy]-17-(cyclopropylmethyl)-4,5a-epoxy-14-hydroxyl-6-(1,3-dioxolan-2-yl)-N-methylmorphinan iodide (N-methyl quaternary derivative of naltrexone), 3-[(tert-butyldimethylsilyl)oxy]-4,5a-epoxy-14-hydroxyl-17-methyl-6-(1,3-dioxolan-2-yl)-N-methylmorphinan iodide (N-methyl quaternary derivative of oxymorphone), 3-[(tert-butyldiphenylsilyl)oxy]-4,5a-epoxy-14-hydroxyl-17-methyl-6-(1,3-dioxolan-2-yl)-N-methylmorphinan iodide (N-methyl quaternary derivative of oxymorphone), 3-[(triisopropylsilyl)oxy]-4,5a-epoxy-14-hydroxyl-17-methyl-6-(1,3-dioxolan-2-yl)-N-methylmorphinan iodide (N-methyl quaternary derivative of oxymorphone), 3-[(tert-butyldimethylsilyl)oxy]-4,5a-epoxy-14-hydroxyl-17-(2-propenyl)-6-(1,3-dioxolan-2-yl)-N-methylmorphinan iodide (N-methyl quaternary derivative of naloxone), 3-[(tert-butyldiphenylsilyl)oxy]-4,5a-epoxy-14-hydroxyl-17-(2-propenyl)-6-(1,3-dioxolan-2-yl)-N-methylmorphinan iodide (N-methyl quaternary derivative of naloxone), 3-[(triisopropylsilyl)oxy]-4,5a-epoxy-14-hydroxyl-17-(2-propenyl)-6-(1,3-dioxolan-2-yl)-N-methylmorphinan iodide (N-methyl quaternary derivative of naloxone), and a single R- or S-type isomer or a mixture thereof. N-methyl quaternary derivative of naltrexone is preferred.

In another aspect, the invention also provides a use of a compound of Formula 1 for preparing a compound of Formula 4,

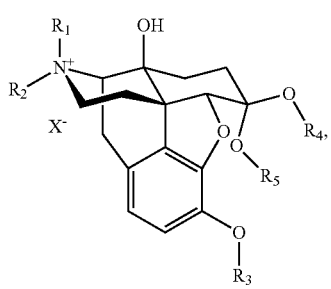

Formula 1

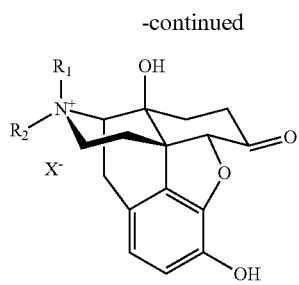

Formula 4 wherein $R_1$ and $R_2$ are each independently a hydrocarbyl or substituted hydrocarbyl, such as a substituted or unsubstituted $C_{1-20}$ hydrocarbyl, particularly a substituted or unsubstituted $C_{1-6}$ hydrocarbyl, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl; preferably, $R_2$ is cyclopropylmethyl when $R_1$ is methyl, or $R_2$ is methyl when $R_1$ is cyclopropylmethyl, $R_3$ is a hydroxyl protecting group or hydrogen, and the hydroxyl protecting group is preferably a substituted or unsubstituted hydrocarbyl, acyl or silyl, such as a substituted or unsubstituted $C_{1-20}$ hydrocarbyl, a substituted or unsubstituted $C_{1-20}$ acyl or a substituted or unsubstituted $C_{1-20}$ hydrocarbyl silyl, particularly a substituted or unsubstituted $C_{1-6}$ hydrocarbyl, a substituted or unsubstituted $C_{1-6}$ acyl or a substituted or unsubstituted $C_{1-6}$ hydrocarbyl silyl, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl; the hydroxyl protecting group is more preferably silyl, such as trimethylsilyl, triethylsilyl, phenyldimethylsilyl, tert-butyldimethylsilyl, tert-butyldiphenylsilyl, triisopropyl silyl, and most preferably is tert-butyldimethylsilyl, $R_4$ and $R_5$ are each independently a substituted or unsubstituted hydrocarbyl, such as a substituted or unsubstituted $C_{1-20}$ hydrocarbyl, particularly a substituted or unsubstituted $C_{1-6}$ hydrocarbyl, alternatively, $R_4$ and $R_5$ form a substituted or unsubstituted 5- or 6-membered ring together with the adjacent "—O—C—O—" moiety, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl; or $R_4=R_5=$—$CH_2$—, with $R_4$ and $R_5$ forming an ethylidene radical together, $X^-$ is an anion, such as fluoride, chloride, bromide, iodide nitrate, sulfate, methanesulfonate, phenylsulfonate, p-toluenesulfonate, trifluoro methanesulfonate or phosphate, or a mixture thereof; typically, $X^-$ is a halide ion, and is preferably methanesulfonate, iodide, bromide, chloride, fluoride, or a mixture thereof.

In one embodiment of the invention, in the use for preparing the compound of Formula 4, the process includes that the compound of Formula 4 is transformed from the compound of Formula 1 by removal of the protecting group with a deprotection agent which is an acid, normally is an inorganic acid, especially halogen acid, preferably is hydrobromic acid, in a solvent, preferably, which solvent is usually alcohol, water, ether or a mixture thereof. The compound of Formula 4 can also be obtained by using tetrabutylammonium fluoride to remove a silyl-ether protecting group, and then hydrolyzing with an acid. The reaction temperature usually varies from −10° C. to 100° C., preferably from 60 to 80° C.

In another aspect, the present invention is to provide a method for preparing a N-alkyl quaternary derivative of tertiary morphinan alkaloid such as the compound of Formula 1, comprising: reacting a compound of Formula 2 with an alkylation agent in an appropriate solvent system to obtain a product (a compound of Formula 1). The solvent system can be a water-containing solvent or water-free solvent system. The water-free solvent system as described herein refers to a solvent system containing less than 1.0 wt % of water, preferably containing less than 0.5 wt % of water. The solvent system can be a water-free solvent system, such as aprotic dipolar solvent, specifically, can be acetone, acetonitrile, dimethyl formamide, dimethyl acetamide, DMSO, N-methyl-pyrrolidinone, or a mixture thereof, and it is preferably acetone, acetonitrile, or DMF. The water-free solvent system can also be a protic solvent, such as formamide, methanol, ethanol or the like. The reaction can be carried out within a relatively broad range of temperature and a relatively broad range of pressure. In one specific embodiment, the reaction can be performed at a temperature ranging from 0 to 120° C., preferably from 0 to 85° C. under the normal pressure or an appropriate pressure (<10 atm). A quantitative yield can almost be obtained in this reaction.

In one embodiment of the invention, tertiary morphinan alkaloid is represented by Formula 2 and the product is represented by Formula 1. The N-alkyl quaternary derivatives of tertiary morphinan alkaloid (Formula 1) are usually prepared by reacting an alkylation agent with a compound of Formula 2 in a water-free solvent system. The alkylation agent is selected from the group consisting of alkyl halide, alkyl sulfonate, alkyl sulfate and alkyl phosphate, preferably an alkyl iodide, alkyl bromide, alkyl methanesulfonate, and more preferably methyl iodide, methyl trifluoromethanesulfonate, methyl bromide.

In still another aspect, the present invention is to provide a method for preparing a compound of Formula 2, comprising: protecting the 6-position ketone group of the compound of Formula 3 with a ketal form and the 3-position hydroxyl thereof with an ester or an ether form, so as to obtain the compound of Formula 2,

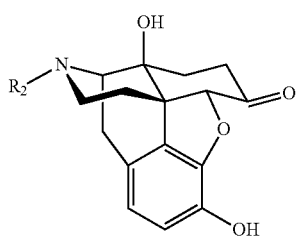

Formula 3 wherein, $R_2$ is a hydrocarbyl or substituted hydrocarbyl, such as a substituted or unsubstituted $C_{1-20}$ hydrocarbyl, particularly a substituted or unsubstituted $C_{1-6}$ hydrocarbyl, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl, and preferably, $R_2$ is cyclopropylmethyl or methyl.

In one embodiment of the invention, the compound of Formula 3 comprises a representative tertiary morphinan alkaloid, especially comprises 17-(cyclopropylmethyl)-4,5a-epoxy-3,14-dihydroxymorphinan-6-one (naltrexone),
4,5a-epoxy-3,14-dihydroxy-17-methylmorphinan-6-one (oxymorphone),
4,5a-epoxy-3,14-dihydroxy-17-(2-propenyl)morphinan-6-one (naloxone).

The present invention also provides a method for preparing a compound of Formula 1, comprising:
a) Protecting the 3-position hydroxyl or 6-position ketone group of the compound of Formula 3,

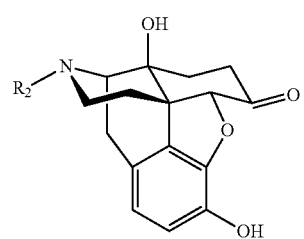

Formula 3 wherein, $R_2$ is a hydrocarbyl or substituted hydrocarbyl, such as a substituted or unsubstituted $C_{1-20}$ hydrocarbyl, particularly a substituted or unsubstituted $C_{1-6}$ hydrocarbyl, wherein the substituent can each independently be selected from the group consisting of fluorine, chlorine, bromine or $C_{1-6}$ hydrocarbyl, which hydrocarbyl can be any suitable alkyl, cycloalkyl, polycyclic alkyl, alkenyl, cycloalkenyl, alkynyl or aryl,
with an ester, ether or ketal form to obtain the compound of Formula 2 as described above;
b) Reacting the compound of Formula 2 as described above with an alkylation agent to obtain the compound of Formula 1 as described above.

In one embodiment of the invention, in the above method for preparing a compound of Formula 1, the compound of Formula 2 is prepared from the compound of Formula 3 via the ketone group protection and the phenolic hydroxyl protection, in which the ketone group protection can be performed before or after the phenolic hydroxyl protection. When the compound of Formula 2 is a ketal silyl protecting hydroxyl compound, it can be prepared from the compound of Formula 3 by firstly protecting the ketone group and then protecting the phenolic hydroxyl.

In one embodiment of the invention, the method comprises a ketal reaction between a compound of Formula 3 and an alcohol under the catalysis of an acid, thereby obtaining a ketal compound of the compound of Formula 3, in which the alcohol is methanol, ethanol or ethylene glycol. In addition to be the solvent, the alcohol is also a reactant; meanwhile, other solvents can be added, such as toluene, benzene and cyclohexane, as a water-carrying agent. The acid is selected from camphorsulfonic acid, p-toluenesulfonic acid, methane sulfonic acid and the like, preferably is camphorsulfonic acid, or p-toluenesulfonic acid. This reaction can be carried out at a temperature varying within a relatively wide range, for example, the reaction temperature can be preferably between 80° C. and 120° C.

After that, the ketal compound of a compound of Formula 3 is reacted with a silyl protecting group agent under the catalysis of a base, so as to obtain the compound of Formula 2, in which the silyl protecting group agent is selected from the group consisting of trimethyl halosilane, triethyl halosilane, phenyldimethyl halosilane, tert-butyldimethyl halosilane, tert-butyldiphenyl halosilane and triisopropylhalosilane, preferably is tert-butyldimethyl halosilane, tert-butyldiphenylhalosilane and triisopropylhalosilane, and the halo can be fluorine, chlorine, bromine or iodine. As an example, the silyl protecting group agent can be trimethyl chlorosilane, triethyl chlorosilane, phenyldimethyl chlorosilane, tert-butyl dimethyl chlorosilane, tert-butyldiphenyl chlorosilane, triisopropylchlorosilane, trimethylbromosilane, triethylbromosilane, phenyldimethylbromosilane, tert-butyldimethylbromosilane, tert-butyldiphenylbromosilane or triisopropylbromosilane. The base is selected from imidazole, triethylamine, DBU, sodium hydride, sodium diisopropylamide, lithium diisopropylamide and the like, and preferably is triethylamine or imidazole. The solvent is DMF, dimethyl acetamide, methylene chloride, toluene, tetrahydrofuran, etc. The reaction temperature can be in the range from −10° C. to 110° C., preferably 20-50° C.

In one embodiment of the invention, the occurrence of N-alkyl quaternary derivative of tertiary morphinan alkaloid-3-phenol alkylation byproduct is avoided, thereby simplifying the process to purify the product. When the documents in the prior art describe an alkylation reaction which is carried out with a tertiary morphinan alkaloid for preparing N-alkyl quaternary derivatives of tertiary morphinan alkaloid, a phenol alkylation reaction takes place inevitably, leading to the presence of tertiary morphinan alkaloid-3-phenol alkylation byproduct in the reaction system. The N-alkyl quaternary derivative of tertiary morphinan alkaloid-3-phenol alkylation byproduct and the tertiary morphinan alkaloid starting material unreacted completely, which make the products hard to purify, need to be precipitated from the reaction system by formation of a sodium salt, in which the base required is a strongly basic agent and easy to cause the product to be partially destroyed and decomposed, thus producing a new byproduct. The technical solution provided by this invention is to carry out the protection before the alkylation and removal of protecting groups are carried out, thereby avoiding the formation of phenol alkylation byproducts and favoring the product purification.

In one embodiment of the invention, by protecting the phenolic hydroxyl of tertiary morphinan alkaloid-3-phenol derivative, its solubility in an organic solvent, such as acetone, acetonitrile or the like is increased, which favors to react completely.

In one embodiment of the invention, a single isomer of N-alkyl quaternary derivative of tertiary morphinan alkaloid with a high purity can be obtained without repeated refining step for many times, because the process comprises: firstly protecting the ketone and phenol group of tertiary morphinan alkaloid, especially after a hindered-type protecting group is introduced, so that a one-way stereoselective reaction is more preferred when the alkylation reaction happens; and after deprotecting, almost pure N-alkyl quaternary derivative of tertiary morphinan alkaloid is produced with only a minor amount of isomers of N-alkyl quaternary derivative of tertiary morphinan alkaloid and without phenol alkylation byproducts which are hard to remove.

In the N-alkyl quaternary derivative of tertiary morphinan alkaloid prepared in the document WO2006127899, for example, the amount of S-isomer, which is relatively hard to remove, is relatively high, and needs to be refined for many times (more than 4 times) before effective removal.

More specifically, when the phenolic hydroxyl and ketone group of naltrexone are both protected, the methylnaltrexone obtained after N-methylation and deprotection is mostly of R-methylnaltrexone with only very few S-methylnaltrexone, which enables 5-methylnaltrexone to be removed almost without refining. In addition, there is no phenol alkylation byproduct. Moreover, all of the intermediates do not need to be purified with a column, which renders the post-treatment easy to handle without a special reaction vessel.

In one embodiment of the invention, a ketal reaction is firstly carried out between naltrexon and an alcohol such as ethylene glycol to give a naltrexone ketal derivative. It is converted into a silane-etherized naltrexone ketal derivative by carrying out a condensation reaction of naltrexone ketal-3-position phenolic hydroxyl with a hindered-typed halosilane compound in the presence of a suitable solvent and a base. This silane-etherized derivative is then easily converted into a silane-etherized quaternary ammonium derivative by reacting with an alkylation agent in a dipolar solvent. R-methylnaltrexone is prepared after deprotection and ion exchange.

PREFERRED EMBODIMENT OF THE INVENTION

The examples given below are for the purpose of better understanding the invention by a person skilled in the art, but do not intend to limit the invention in any way.

EXAMPLE 1

Preparation of 17-(cyclopropylmethyl)-4,5a-epoxy-3,14-dihydroxy-6-(1,3-dioxolan-2-yl)-morphinan

EXAMPLE 1-1

To 800 ml of toluene, naltrexone (10 g, 29.3 mmol), camphorsulfonic acid (9.8 g, 42.2 mmol) and ethylene glycol (40 ml, 742 mmol) were added, and the whole system was refluxed to separate water overnight. After the reaction was complete, $NaHCO_3$ powder was added to the reaction solution, and the solvent was evaporated under reduced pressure with residue dissolved in trichloromethane. The organic layer was washed with saturated $NaHCO_3$ solution and saturated brine, and dried over anhydrous sodium sulfate. Upon concentrating the organic layer, a white-like solid was produced. The solid was recrystallized from ethyl acetate to give a white crystal of 10.3 g. Yield: 91%. Melting point: 218-220° C.

EXAMPLE 1-2

To 800 ml of toluene, Naltrexone (10 g, 29.3 mmol), p-toluenesulfonic acid (7.2 g, 42.2 mmol) and ethylene glycol (40 ml, 742 mmol) were added, and the whole system was refluxed to separate water overnight. After the reaction was complete, $NaHCO_3$ powder was added to the reaction solution, and the solvent was evaporated under reduced pressure with residue dissolved in trichloromethane. The organic layer was washed with saturated $NaHCO_3$ solution and saturated brine, and dried over anhydrous sodium sulfate. Upon concentrating the organic layer, a white-like solid was produced. The solid was recrystallized from ethyl acetate to give a white crystal of 10.7 g. Yield: 95%. Melting point: 217-221° C.

EXAMPLE 1-3

To 1000 ml of cyclohexane, naltrexone (10 g, 29.3 mmol), camphorsulfonic acid (9.8 g, 42.2 mmol) and ethylene glycol (20 ml, 371 mmol) were added, and the whole system was refluxed to separate water overnight. After the reaction was complete, $NaHCO_3$ powder was added to the reaction solution, and the solvent was evaporated under reduced pressure with residue dissolved in trichloromethane. The organic layer was washed with saturated NaHCO$_3$ solution and saturated brine, and dried over anhydrous sodium sulfate. Upon concentrating the organic layer, a white-like solid was produced. The solid thus obtained was recrystallized from ethyl acetate to give a white crystal of 9.6 g. Yield: 85%. Melting point: 217-220° C.

EXAMPLE 2-1

Preparation of 3-[(tert-butyldimethylsilyl)oxy]-17-(cyclopropylmethyl)-4,5a-epoxy-14-hydroxyl-6-(1,3-dioxolan-2-yl)morphinan 17-(cyclopropylmethyl)-4,5a-epoxy-3,14-dihydroxy-6-(1,3-dioxolan-2-yl)morphinan (3.85 g, 10 mmol) was dissolved in 10 ml of DMF, then imidazole (0.68 g, 10 mmol) and tert-butyl dimethyl chlorosilane (1.5 g, 10 mmol) were added with stirring. The whole system was reacted at a temperature ranging from 20° C. to 25° C. for 40 min. After the reaction was complete, water was added to the system and the resultant mixture was extracted with diethyl ether for 3 times. The organic layer was washed with water, dried over anhydrous magnesium sulfate, and concentrated for crystallization to afford a white solid of 4.0 g. Yield: 80%. Melting point: 107.7-109.3° C.

$^1$HNMR δ6.48-6.54(2H), δ5.90(1H), δ4.35(1H), δ3.97 (1H), 63.80(2H), 63.66(1H), 63.31-3.60(2H), 62.97(1H), δ2.31-2.60(2H), δ2.31(2H), δ2.15(1H), δ1.98(2H), δ1.39 (3H), δ1.15(1H), δ0.95(9H), δ0.80-0.90(2H), δ0.44(2H), δ0.12(6H)

EXAMPLE 2-2

Preparation of 3-[(tert-butyldiphenylsilyl)oxy]-17-(cyclopropylmethyl)-4,5a-epoxy-14-hydroxyl-6-(1,3-dioxolan-2-yl)morphinan 17-(cyclopropylmethyl)-4,5a-epoxy-3,14-dihydroxy-6-(1,3-dioxolan-2-yl)morphinan (3.85 g, 10 mmol) was dissolved in 10 ml of THF, then triethylamine (1.01 g, 10 mmol) and tert-butyldiphenyl chlorosilane (2.75 g, 10 mmol) were added with stirring. The whole system was reacted at a temperature ranging from 45° C. to 50° C. for 2 hours. After the reaction was complete, water was added to the system and the resultant mixture was extracted with diethyl ether for 3 times. The organic layer was washed with water, dried over anhydrous magnesium sulfate, and concentrated for crystallization to afford a white solid.

$^1$HNMR δ7.55(2H), δ6.48-6.54(2H), δ5.90(1H), δ4.35 (1H), δ3.97(1H), δ3.80(2H), δ3.66(1H), δ3.31-3.60(2H), δ2.97(1H), δ2.31-2.60(2H), δ2.31(2H), δ2.15(1H), δ1.98 (2H), δ1.39(3H), δ1.15(1H), δ0.95(9H), δ0.80-0.90(2H), δ0.44(2H)

EXAMPLE 2-3

Preparation of 3-[(triisopropylsilyl)oxy]-17-(cyclopropylmethyl)-4,5a-epoxy-14-hydroxyl-6-(1,3-dioxolan-2-yl)morphinan 17-(cyclopropylmethyl)-4,5a-epoxy-3,14-dihydroxy-6-(1,3-dioxolan-2-yl)morphinan (3.85 g, 10 mmol) was dissolved in 20 ml of methylene chloride, then imidazole (0.68 g, 10 mmol) and triisopropylchlorosilane (1.92 g, 10 mmol) were added with stirring. The whole system was refluxed to react for 4 hours. After the reaction was complete, water was added for extraction and then extracted with methylene chloride for 3 times. The organic layer was washed with water, dried over anhydrous magnesium sulfate, and concentrated for crystallization to afford a white solid.

$^1$HNMR δ6.48-6.54(2H), δ5.90(1H), δ4.35(1H), δ3.97 (1H), δ3.80(2H), δ3.66(1H), δ3.31-3.60(2H), δ2.97(1H), δ2.31-2.60(2H), δ2.31(2H), δ2.15(1H), δ1.98(2H), δ1.8 (3H), δ1.39(3H), δ1.15(1H), δ0.92(18H), δ0.80-0.90(2H), δ0.44(2H)

EXAMPLE 3-1

Preparation of 3-[(tert-butyldimethylsilyl)oxy]-17-(cyclopropylmethyl)-4,5a-epoxy-14-hydroxyl-6-(1,3-dioxolan-2-yl)-N-methylmorphinan iodide 3-[(tert-butyldimethylsilyl)oxy]-17-(cyclopropylmethyl)-4,5a-epoxy-14-hydroxyl-6-(1,3-dioxolan-2-yl)morphinan (5 g, 0.01 mmol) was dissolved in 20 ml of DMF, and 1 ml of methyl iodide was added. The reaction was carried out overnight at a temperature controlled to be 35-40° C. After the reaction was complete, the solvent was evaporated off under reduced pressure to afford a light-yellow solid with an almost quantitative yield.

$^1$HNMR δ6.79(2H), δ5.91(1H), δ4.56(1H), δ3.96-3.98 (1H), δ3.80-3.88(4H), δ3.96-3.74(1H), δ3.69(3H), δ3.48-3.52(1H), δ3.29-3.31(1H), δ3.04-3.09(1H), δ2.89-2.93(1H), δ2.68-2.74(1H), δ2.58-2.65(1H), δ2.05-2.10(1H), δ1.68-1.71(1H), δ1.38-1.49(3H), δ1.22-1.23(1H), δ0.95(9H), δ0.75-0.80(1H), δ0.67-0.72(1H), δ0.60-0.64(1H), δ0.34-0.39(1H), δ0.16-0.19(6H)

$^{13}$CNMR δ147.7(1C), δ137.6(1C), δ129.1(1C), δ121.6 (1C), δ119.2(1C), δ107.6(1C), δ91.8(1C), δ71.8(1C), δ71.2 (1C), δ70.8(1C), δ65.7(1C), δ64.1(1C), δ57.1(1C), δ53.4 (1C), δ46.2(1C), δ29.7(1C), δ27.9(1C), δ27.4(1C), δ25.4 (1C), δ17.8(1C), δ5.8(1C), δ3.8(1C), δ2.7(1C), δ−4.6/−4.9 (5C)

EXAMPLE 3-2

Preparation of 3-[(tert-butyldiphenylsilyl)oxy]-17-(cyclopropylmethyl)-4,5a-epoxy-14-hydroxyl-6-(1,3-dioxolan-2-yl)-N-methylmorphinan methanesulfonate 3-[(tert-butyldiphenylsilyl)oxy]-17-(cyclopropylmethyl)-4,5a-epoxy-14-hydroxyl-6-(1,3-dioxolan-2-yl)morphinan (6.2 g, 0.01 mmol) was dissolved in 25 ml of acetonitrile, and 1 ml of methyl methanesulfonate was added. The reaction was carried out overnight at a temperature controlled to be reflux. After the reaction was complete, the solvent was evaporated off under reduced pressure to afford a light-yellow viscous solid with an almost quantitative yield.

$^1$HNMR δ7.55(2H), δ6.48-6.54(2H), δ5.90(1H), δ4.35 (1H), δ3.97(1H), δ3.80(2H), δ3.69(3H), δ3.66(1H), δ3.31-3.60(2H), δ2.97(1H), δ2.31-2.60(2H), δ2.31(2H), δ2.15 (1H), δ1.98(2H), δ1.39(3H), δ1.15(1H), δ0.95(9H), δ0.80-0.90(2H), δ0.44(2H)

EXAMPLE 3-3

Preparation of 3-[(triisopropylsilyl)oxy]-17-(cyclopropylmethyl)-4,5a-epoxy-14-hydroxyl-6-(1,3-dioxolan-2-yl)-N-methylmorphinan trifluoromethanesulfonate 3-[(triisopropylsilyl)oxy]-17-(cyclopropylmethyl)-4,5a-epoxy-14-hydroxyl-6-(1,3-dioxolan-2-yl)-morphinan (5.4 g, 0.01 mmol) was dissolved in 25 ml of acetone, and 1 ml of methyl trifluoromethanesulfonate was added. The reaction was carried out overnight at a temperature controlled to be 0° C. After the reaction was complete, the solvent was evaporated off under reduced pressure to afford a reddish-brown viscous solid.

$^{1}$HNMR δ6.48-6.54(2H), δ5.90(1H), δ4.35(1H), δ3.97 (1H), δ3.80(2H), δ3.69(3H), δ3.66(1H), δ3.31-3.60(2H), δ2.97(1H), δ2.31-2.60(2H), δ2.31(2H), δ2.15(1H), δ1.98 (2H), δ1.8(3H), δ1.39(3H), δ1.15(1H), δ0.92(18H), δ0.80-0.90(2H), δ0.44(2H)

EXAMPLE 3-4

Preparation of 3-[(tert-butyldimethylsilyl)oxy]-17-(cyclopropylmethyl)-4,5a-epoxy-14-hydroxyl-6-(1,3-dioxolan-2-yl)-N-methylmorphinan bromide 3-[(tert-butyldimethylsilyl)oxy]-17-(cyclopropylmethyl)-4,5a-epoxy-14-hydroxyl-6-(1,3-dioxolan-2-yl)morphinan (2.5 g, 0.005 mmol) was dissolved in 10 ml of NMP. Methyl bromide was cooled in an iced salt bath, 1 ml carefully metered was immediately added to 5 ml of NMP previously frozen so as to dilute, and then added to the reaction solution with a closed balloon. The reaction was carried out overnight at a temperature controlled to be 55-60° C. After the reaction was complete, the solvent was evaporated off under reduced pressure to afford a light-yellow solid with an almost quantitative yield.

LC/MS: 594

EXAMPLE 4-1

Preparation of R—N-methylnaltrexone iodide/bromide

3-[(tert-butyldimethylsilyl)oxy]-17-(cyclopropylmethyl)-4,5a-epoxy-14-hydroxyl-6-(1,3-dioxolan-2-yl)-N-methyl-morphinan iodide (21.14 g, 33 mmol) was added to a solution containing 150 ml of methanol and 200 ml of 10% hydrobromic acid, and heated to 60~65° C. to react for 6 hours. After the end of the reaction was reached by TCL monitoring, it was concentrated to dry under reduced pressure. To the residue, acetonitrile/water was added for cooling crystallization, to give a light-yellow crystalline solid of 11.5 g.

EXAMPLE 4-2

3-[(tert-butyldimethylsilyl)oxy]-17-(cyclopropylmethyl)-4,5a-epoxy-14-hydroxyl-6-(1,3-dioxolan-2-yl)-N-methyl-morphinan iodide (21.14 g, 33 mmol) was dissolved in 150 ml of mixed solvent of tetrahydrofuran and water (THF:water/5:1), added 45 ml of 48% hydrobromic acid and 105 ml of water, and heated to reflux to react for 5 hours. After the end of the reaction was reached by TCL monitoring, it was concentrated to dry under reduced pressure. To the residue, acetonitrile/water was added for cooling crystallization, to give a light-yellow crystalline solid of 11.8 g.

EXAMPLE 5

Preparation of R—N-methylnaltrexone bromide 11.8 g N-methylnaltrexone iodide/bromide was dissolved in 250 ml water. The resultant solution passed through an ion exchange chromatography column packed with 85 g of strongly basic bromide exchanger having an exchange capacity of 0.513Val, which was then washed with 750 ml of water. The filtrate was collected and concentrated at 70° C. under reduced pressure. The residue was dissolved in 100 ml of methanol, and 50 ml of diethyl ether was added to precipitate a white solid of 10.1 g with a yield of 85 wt %, a HPLC purity of 99.7% and a melting point of 260° C.

$^{1}$HNMR δ9.52(1H), δ6.68(2H), δ6.41(1H), δ4.93(1H), δ4.03-4.04(1H), δ3.89-3.93(1H), δ3.69(3H), δ3.29-3.35 (1H), δ2.89-3.08(3H), δ2.79-2.80(2H), δ2.05-2.11(2H), δ1.54-1.64(2H), δ1.20-1.24(1H), δ0.75-0.79(1H), δ0.67-0.73(1H), δ0.60-0.65(1H), δ0.36-0.40(1H)

$^{13}$CNMR δ207.5(1C), δ143.6(1C), δ140.4(1C), δ127.7 (1C), δ120.3(1C), δ119.8(1C), δ118.1(1C), δ88.5(1C), δ71.7 (1C), δ70.8(2C), δ56.6(1C), δ52.8(1C), δ48.3(1C), δ34.8 (1C), δ32.0(1C), δ527.3(1C), δ24.4(1C), δ5.7(1C), δ3.8(1C), δ2.7(1C)

EXAMPLE 6

Preparation of 17-(cyclopropylmethyl)-4,5a-epoxy-3,14-dihydroxy-6-(1,3-dioxolan-2-yl)-N-methylmorphinan fluoride/bromide 3-[(tert-butyldimethylsilyl)oxy]-17-(cyclopropylmethyl)-4,5a-epoxy-14-hydroxyl-6-(1,3-dioxolan-2-yl)-N-methyl-morphinan iodide (1 g, 1.5 mmol) was dissolved in THF (10 ml), and a solution of 1M tetrabutylammonium fluoride in tetrahydrofuran (2.3 ml) was added and stirred at room temperature for 90 min. After the reaction was complete, it was concentrated under reduced pressure and recrystallized from methanol/diethyl ether to give a white solid of 0.7 g.

$^{1}$HNMR δ9.52(1H), δ6.68(2H), δ6.41(1H), δ4.93(1H), δ4.03-4.04(1H), δ3.89-3.93(1H), 3.80-3.88(4H), δ3.69(3H), δ3.29-3.35(1H), δ2.89-3.08(3H), δ2.79-2.80(2H), δ2.05-2.11(2H), δ1.54-1.64(2H), δ1.20-1.24(1H), δ0.75-0.79(1H), δ0.67-0.73(1H), δ0.60-0.65(1H), δ0.36-0.40(1H)

The invention claimed is:
1. A morphinan derivative of Formula 1,

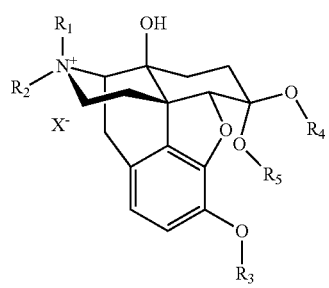

Formula 1 wherein:
$R_1$ and $R_2$ are each independently a hydrocarbyl or substituted hydrocarbyl,
$R_3$ is a hydroxyl protecting group or hydrogen,
$R_4$ and $R_5$ are each independently a substituted or unsubstituted hydrocarbyl,
$X^-$ is an anion.
2. The morphinan derivative of claim 1, wherein $R_1$ and $R_2$ of Formula 1 are each independently methyl, ethyl, propyl, allyl (—$CH_2CH$=$CH_2$), cyclopropylmethyl or chloroallyl.
3. The morphinan derivative of claim 1, wherein the hydroxyl protecting group represented by $R_3$ is a substituted or unsubstituted hydrocarbyl, acyl or silyl.

4. The morphinan derivative of claim 3, wherein the silyl represented by $R_3$ is selected from the group consisting of trimethylsilyl, triethylsilyl, phenyldimethylsilyl, tert-butyldimethylsilyl, tert-butyldiphenylsilyl and triisopropylsilyl.

5. The morphinan derivative of claim 1, wherein $R_4=R_5=$—$CH_2$—, with $R_4$ and $R_5$ together forming an ethylidene radical.

6. The morphinan derivative of claim 1, wherein $X^-$ is fluoride, chloride, bromide, iodide nitrate, sulfate, methanesulfonate, phenylsulfonate, p-toluenesulfonate, trifluoro methanesulfonate or phosphate, or a combination thereof.

7. The morphinan derivative of claim 1, which is 3-[(tert-butyldimethylsilyl)oxy]-17-(cyclopropylmethyl)-4,5a-epoxy-14-hydroxyl-6-(1,3-dioxolan-2-yl)-N-methylmorphinan iodide (N-methyl quaternary derivative of naltrexone), 3-[(tert-butyldiphenylsilyl)oxy]-17-(cyclopropylmethyl)-4,5a-epoxy-14-hydroxyl-6-(1,3-dioxolan-2-yl)-N-methylmorphinan iodide (N-methyl quaternary derivative of naltrexone), 3-[(triisopropylsilyl)oxy]-17-(cyclopropylmethyl)-4,5a-epoxy-14-hydroxyl-6(1,3-dioxolan-2-yl)-N-methylmorphinan iodide (N-methyl quaternary derivative of naltrexone), 3-[(tert-butyldimethylsilyl)oxy]-4,5a-epoxy-14-hydroxyl-17-methyl-6-(1,3-dioxolan-2-yl)-N-methylmorphinan iodide (N-methyl quaternary derivative of oxymorphone), 3-[(tert-butyldiphenylsilyl)oxy]-4,5a-epoxy-14-hydroxyl-17-methyl-6-(1,3-dioxolan-2-yl)-N-methylmorphinan iodide (N-methyl quaternary derivative of oxymorphone), 3-[(triisopropylsilyl)oxy]-4,5a-epoxy-14-hydroxyl-17-methyl-6-(1,3-dioxolan-2-yl)-N-methylmorphinan iodide (N-methyl quaternary derivative of oxymorphone), 3-[(tert-butyldimethylsilyl)oxy]-4,5a-epoxy-14-hydroxyl-17-(2-propenyl)-6-(1,3-dioxolan-2-yl)-N-methylmorphinan iodide (N-methyl quaternary derivative of naloxone), 3-[(tert-butyldiphenylsilyl)oxy]-4,5a-epoxy-14-hydroxyl-17-(2-propenyl)-6-(1,3-dioxolan-2-yl)-N-methylmorphinan iodide (N-methyl quaternary derivative of naloxone), 3-[(triisopropylsilyl)oxy]-4,5a-epoxy-14-hydroxyl-17-(2-propenyl)-6-(1,3-dioxolan-2-yl)-N-methylmorphinan iodide (N-methyl quaternary derivative of naloxone), a single R-type or single S-type thereof or a mixture thereof.

8. A compound of Formula 2,

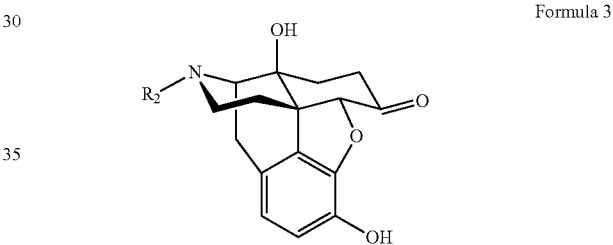

Formula 2 wherein
$R_2$ is a hydrocarbyl or substituted hydrocarbylsilyl, R3 is silyl,
$R_4=R_5=$—$CH_2$—, then $R_4$ and $R_5$ together form an ethylidene radical.

9. The compound of claim 8, wherein $R_2$ is methyl, ethyl, propyl, allyl (—$CH_2CH=CH_2$), chloroallyl, cyclopropylmethyl, cyclobutylmethyl or propargyl.

10. The compound of claim 8, wherein the silyl represented by $R_3$ is selected from the group consisting of trimethylsilyl, triethylsilyl, phenyldimethylsilyl, tert-butyldimethylsilyl, tert-butyldiphenylsilyl and triisopropylsilyl, preferably tert-butyldimethylsilyl.

11. The compound of claim 8, which is 3-[(tert-butyldimethylsilyl)oxy]-17-(cyclopropylmethyl)-4,5a-epoxy-14-hydroxyl-6-(1,3-dioxolan-2-yl)morphinan, 3-[(tert-butyldiphenylsilyl)oxy]-17-(cyclopropylmethyl)-4,5a-epoxy-14-hydroxyl-6-(1,3-dioxolan-2-yl)morphinan, 3-[(triisopropylsilyl)oxy]-17-(cyclopropylmethyl)-4,5a-epoxy-14-hydroxyl-6-(1,3-dioxolan-2-yl)morphinan, 3-[(tert-butyldimethylsilyl)oxy]-4,5a-epoxy-14-hydroxyl-17-methyl-6-(1,3-dioxolan-2-yl)-morphinan, 3-[(tert-butyldiphenylsilyl)oxy]-4,5a-epoxy-14-hydroxyl-17-methyl-6-(1,3-dioxolan-2-yl)-morphinan, 3-[(triisopropylsilyl)oxy]-4,5a-epoxy-14-hydroxyl-17-methyl-6-(1,3-dioxolan-2-yl)-morphinan, 3-[(tert-butyldimethylsilyl)oxy]-4,5a-epoxy-14-hydroxyl-17-(2-propenyl)-6-(1,3-dioxolan-2-yl)-morphinan, 3-[(tert-butyldiphenylsilyl)oxy]-4,5a-epoxy-14-hydroxyl-17-(2-propenyl)-6-(1,3-dioxolan-2-yl)-morphinan, or 3-[(triisopropylsilyl)oxy]-4,5a-epoxy-14-hydroxyl-17-(2-propenyl)-6-(1,3-dioxolan-2-yl)-morphinan.

12. A method for preparing the morphinan derivative of claim 1, comprising:
(a) Protecting the 3-position hydroxyl or 6-position ketone group of the compound of Formula 3

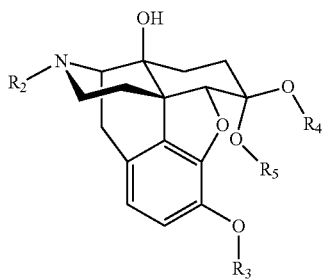

Formula 3 wherein $R_2$ in Formula 3 is as defined above for $R_2$ in Formula 1 in claim 1, with an ester, ether or ketal form to obtain the compound of Formula 2;
(b) reacting the compound of Formula 2 with an alkylation agent to obtain the compound of Formula 1

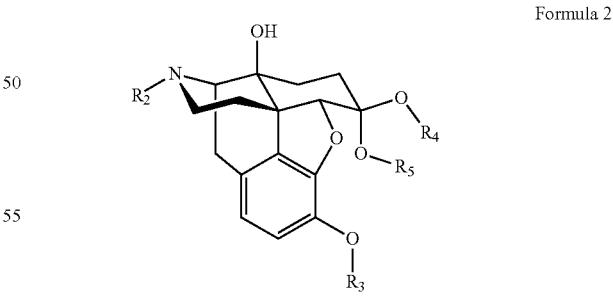

Formula 2 wherein:
$R_2$ is a hydrocarbyl or substituted hydrocarbylsilyl,
$R_3$ is a substituted or unsubstituted hydrocarbyl, acyl or silyl, and
$R_4=R_5=$—$CH_2$—, with $R_4$ and $R_5$ together forming an ethylidene radical.

13. The method of claim 12, wherein a ketal reaction is firstly carried out between a compound of Formula 3 and an alcohol under the catalysis of an acid to obtain a ketal compound of the compound of Formula 3, and then the ketal compound reacts with a silyl protecting group agent under the catalysis of a base to obtain the compound of Formula 2.

14. The method of claim 13, wherein the alcohol is methanol, ethanol, ethylene glycol or a mixture thereof; the acid is camphorsulfonic acid, p-toluenesulfonic acid, methane sulfonic acid or a mixture thereof; the ketal reaction is carried out at a temperature ranging from 80° C. to 120° C.; the silyl protecting group agent is trimethyl halosilane, triethyl halosilane, phenyldimethyl halosilane, tert-butyldimethyl halosilane, tert-butyldiphenyl halosilane or triisopropylhalosilane, preferably tert-butyldimethyl halosilane, tert-butyldiphenylhalosilane or triisopropylhalosilane; and the halo is fluorine, chlorine, bromine or iodine; and the base is imidazole, triethylamine, DBU, sodium hydride, sodium diisopropylamide, lithium diisopropylamide or a mixture thereof; and the base catalytic reaction is carried out at a temperature ranging from −10° C. to 110° C.

15. The method of claim 14, wherein the alkylation agent is alkyl halide, alkyl sulfonate, alkyl sulfate, or alkyl phosphate, preferably alkyl iodide, alkyl bromide or alkyl methanesulfonate, more preferably methyl methanesulfonate, methyl trifluoromethanesulfonate, methyl iodide, methyl bromide or a mixture thereof, and the reaction of the compound of Formula 2 and the alkylation agent is carried out at a temperature ranging from 0° C. to 120° C.

16. A method for preparing a compound of Formula 4, comprising:
converting into the compound of Formula 4 from the compound of Formula 1 of claim 1 by removing $R_3$, $R_4$ and $R_5$

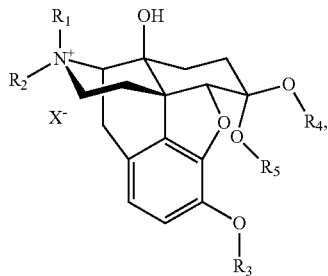

Formula 1

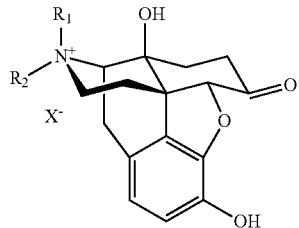

Formula 4 wherein $R_1$, $R_2$, $R_3$, $R_4$ and $R_5$ are as defined in claim 1.

17. The method of claim 16, wherein the removal is achieved through a hydrolysis reaction catalyzed by an acid, and the hydrolysis reaction is carried out at a temperature ranging from −10° C. to 100° C.

18. The method of claim 17, wherein the acid is halogen acid.

* * * * *